United States Patent
Chen

(10) Patent No.: US 9,220,610 B2
(45) Date of Patent: Dec. 29, 2015

(54) TEXTURED IMPLANT DEVICE HAVING SERIES EXTENDIBLE BLADES

(71) Applicant: Kuei Jung Chen, Changhua Hsien (TW)

(72) Inventor: Kuei Jung Chen, Changhua Hsien (TW)

( * ) Notice: Subject to any disclaimer, the term of this patent is extended or adjusted under 35 U.S.C. 154(b) by 279 days.

(21) Appl. No.: 13/847,525

(22) Filed: Mar. 20, 2013

(65) Prior Publication Data

US 2014/0288653 A1 Sep. 25, 2014

(51) Int. Cl.
*A61F 2/44* (2006.01)
*A61F 2/30* (2006.01)

(52) U.S. Cl.
CPC .......... *A61F 2/447* (2013.01); *A61F 2/446* (2013.01); *A61F 2002/3085* (2013.01); *A61F 2002/30112* (2013.01); *A61F 2002/30507* (2013.01); *A61F 2002/30538* (2013.01); *A61F 2002/30579* (2013.01); *A61F 2002/30904* (2013.01)

(58) Field of Classification Search
USPC ................................. 623/17.11, 17.15, 17.16
See application file for complete search history.

(56) References Cited

U.S. PATENT DOCUMENTS

| | | | |
|---|---|---|---|
| 5,554,191 A * | 9/1996 | Lahille et al. .............. | 623/17.11 |
| 5,800,550 A * | 9/1998 | Sertich ....................... | 623/17.16 |
| 5,865,848 A | 2/1999 | Baker | |
| 5,888,227 A | 3/1999 | Cottle | |
| 5,989,289 A | 11/1999 | Coates et al. | |
| 6,139,579 A | 10/2000 | Steffee et al. | |
| 6,176,882 B1 * | 1/2001 | Biedermann et al. ...... | 623/17.15 |
| 6,179,873 B1 * | 1/2001 | Zientek ...................... | 623/17.11 |
| 6,511,509 B1 | 1/2003 | Ford et al. | |
| 6,527,803 B1 * | 3/2003 | Crozet et al. ............... | 623/17.11 |
| 6,685,742 B1 * | 2/2004 | Jackson ...................... | 623/17.11 |
| 6,821,298 B1 * | 11/2004 | Jackson ...................... | 623/17.15 |
| 7,727,280 B2 * | 6/2010 | McLuen ..................... | 623/17.16 |
| 8,523,946 B1 * | 9/2013 | Swann ........................ | 623/17.16 |
| 8,597,360 B2 * | 12/2013 | McLuen et al. ............. | 623/17.16 |
| 8,845,731 B2 * | 9/2014 | Weiman ...................... | 623/17.15 |
| 8,926,704 B2 * | 1/2015 | Glerum et al. ............. | 623/17.16 |
| 8,968,405 B2 * | 3/2015 | Kirwan et al. ............. | 623/17.16 |
| 2010/0185289 A1 * | 7/2010 | Kirwan et al. ............. | 623/17.11 |
| 2012/0226357 A1 * | 9/2012 | Varela ........................ | 623/17.16 |

* cited by examiner

*Primary Examiner* — Jerry Cumberledge
*Assistant Examiner* — Nicholas Plionis
(74) *Attorney, Agent, or Firm* — Charles E. Baxley

(57) ABSTRACT

A textured bone graft or implant device includes a housing member having a bore at one end and a conduit at the other, an actuator engaged in the conduit of the housing member, and a screw engaged in the bore of the housing member and engaged with the actuator, and the housing member includes two sections each having one or more grooves for forming two or more blades each of which include a guiding member extended into the conduit of the housing member for selectively engaging with the actuator, the actuator is engaged with a closer guiding member before the other for forcing the blades to move radially and outwardly of the housing member in sequence.

6 Claims, 8 Drawing Sheets

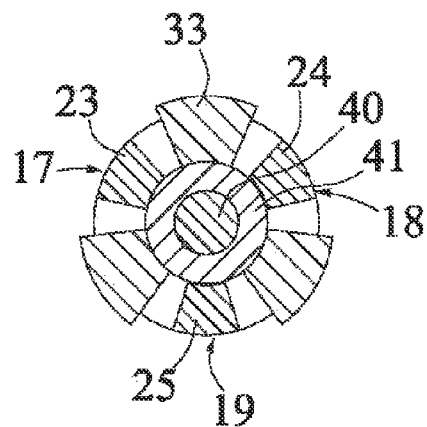 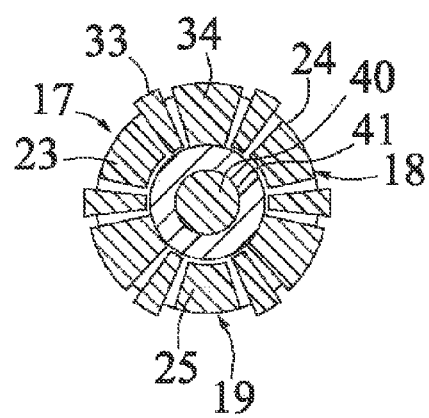
FIG. 7  FIG. 8
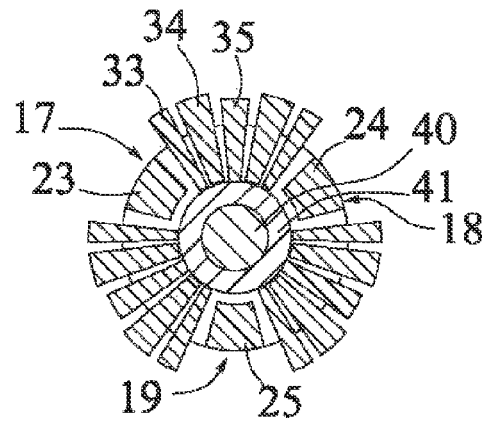
FIG. 9
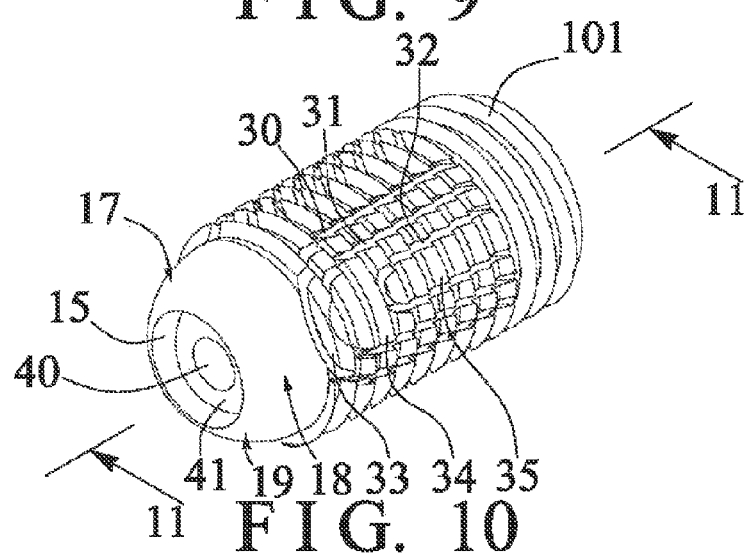
FIG. 10

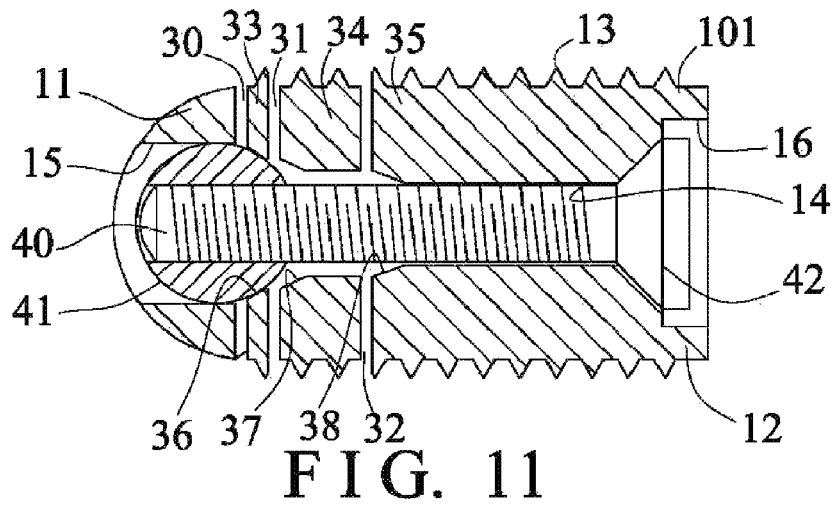
F I G. 11
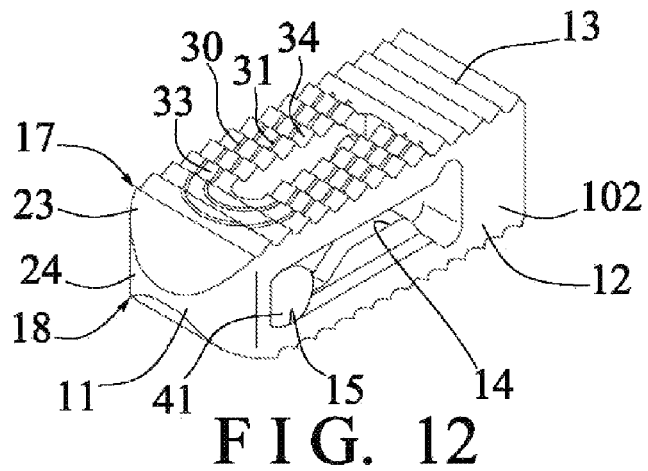
F I G. 12
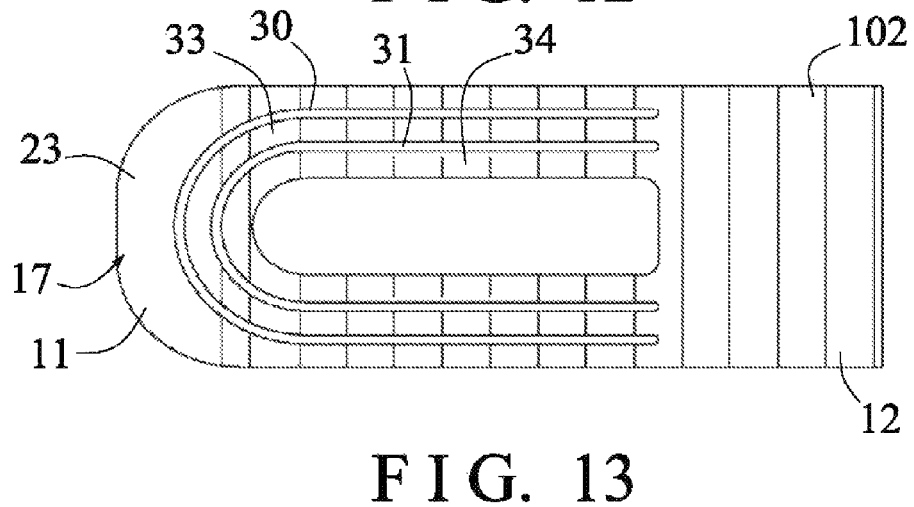
F I G. 13

TEXTURED IMPLANT DEVICE HAVING SERIES EXTENDIBLE BLADES

BACKGROUND OF THE INVENTION

1. Field of the Invention

The present invention relates to a textured bone graft or implant device, and more particularly to a textured bone graft or implant device including an improved structure for being suitably filled or fitted or engaged into the bone materials or members of the human or user and for repairing bone defects, such as the damaged or degenerated spinal disc in a spinal column or vertebrae of a human or user, or the like.

2. Description of the Prior Art

Typical bone grafts, intervertebral implants, intervertebral spacers, textured bone graft devices or the like have been developed and provided for being filled or fitted or engaged into the bone materials or members of the human or user and for repairing bone defects, such as the damaged or degenerated spinal disc in a spinal column or vertebrae of a human or user, or the like, and comprise a constructed or textured spatial member for fitting or engaging into the bone materials or members of the user and for repairing bone defects.

For example, U.S. Pat. No. 5,888,227 to Cottle, U.S. Pat. No. 5,989,289 to Coates et al., U.S. Pat. No. 6,139,579 to Steffee et al., and U.S. Pat. No. 6,511,509 to Ford et al. disclose several of the typical bone grafts, intervertebral implants, intervertebral spacers, textured bone graft devices or the like and each also comprising a constructed or textured spatial member, such as an artificial spinal disc prosthesis, or the like for fitting or engaging into the bone materials or members, such as the damaged or degenerated spinal column or vertebrae or spinal disc of the human or user.

However, the damaged or degenerated spinal columns or vertebrae or spinal discs of the human or users may include a size or dimension or height or depth or width different from each other, but the conventional or typical bone grafts, intervertebral implants, intervertebral spacers, textured bone graft devices or the like comprise a constructed or textured spatial member that includes a solid and stable structure and that may not be adjusted to suitably fill or fit or engage into the damaged or degenerated spinal columns or vertebrae or spinal discs having different sizes or dimensions or heights or depths or widths. U.S. Pat. No. 5,554,191 to Lahille et al. and U.S. Pat. No. 5,865,848 to Baker disclose the other typical bone grafts, intervertebral implants, intervertebral spacers, textured bone graft devices or the like each comprising a constructed or textured spatial member having two movable elements adjustable or movable relative to each other for suitably filling or fitting or engaging into the damaged or degenerated spinal columns or vertebrae or spinal discs having different sizes or dimensions or heights or depths or widths.

However, the damaged or degenerated spinal columns or vertebrae or spinal discs not only include different sizes or dimensions or heights or depths or widths but also include different shapes such that the adjustable or movable elements may not be used or adjusted to suitably fill or fit or engage into the damaged or degenerated spinal columns or vertebrae or spinal discs having different sizes or dimensions or heights or depths or widths and having different shapes.

The present invention has arisen to mitigate and/or obviate the afore-described disadvantages of the conventional textured bone graft or implant devices.

SUMMARY OF THE INVENTION

The primary objective of the present invention is to provide a textured bone graft or implant device including an improved structure for being suitably filled or fitted or engaged into the bone materials or members of the human or user and for repairing bone defects, such as the damaged or degenerated spinal disc in a spinal column or vertebrae of a human or user, or the like.

In accordance with one aspect of the invention, there is provided a textured implant device comprising a housing member including a first end and a second end, and including a longitudinal bore formed in the housing member and located closer to the second end, and including a longitudinal conduit formed in the housing member and located closer to the first end but not formed through the second end of the housing member, and the conduit of the housing member including an inner diameter greater than that of the bore of the housing member, an actuator slidably received and engaged in the conduit of the housing member, and a screw rotatably received and engaged in the bore of the housing member and threaded and engaged with the actuator, and the housing member including a first section and a second section equally spaced from each other, and including at least one groove formed in each section of the housing member for forming and defining a first blade and a second blade in each section of the housing member, and the first and the second blades each including a guiding member extended into the conduit of the housing member for selectively engaging with the actuator, the guiding member of the first blade being located closer to the actuator than the guiding member of the second blade, and the actuator being contacted and engaged with the guiding member of the first blade before contacting or engaging with the guiding member of the second blade in order to force the first blade to move radially and outwardly of the housing member before forcing the second blade to move radially and outwardly of the housing member.

The groove of the housing member is U-shaped for forming and defining a U-shaped first blade and a U-shaped second blade in each section of the housing member. The first end of the housing member preferably includes a rounded structure for being easily and quickly engaged into the space between two vertebral bodies or the like.

The housing member includes at least one slot formed therein and located closer to the first end, but not formed through the second end of the housing member for forming and defining the equally spaced first and second sections of the housing member and for forming and defining a first resilient branch and a second resilient branch in the first and the second sections of the housing member respectively.

Further objectives and advantages of the present invention will become apparent from a careful reading of the detailed description provided hereinbelow, with appropriate reference to the accompanying drawings.

BRIEF DESCRIPTION OF THE DRAWINGS

FIGS. 7, 8, 9 are further cross sectional views of the textured implant device, taken along lines 7-7, 8-8, 9-9 of FIGS. 3, 4, 5 respectively;

FIG. 10 is another perspective view of the textured implant device similar to FIG. 1, illustrating the other arrangement of the textured implant device;

FIG. 11 is a cross sectional view of the textured implant device, taken along lines 11-11 of FIG. 10;

FIG. 12 is a further perspective view similar to FIGS. 1 and 10, illustrating the further arrangement of the textured implant device;

FIG. 13 is a top plan schematic view of the textured implant device as shown in FIG. 12;

FIG. 15 is another side plan schematic view similar to FIG. 14, illustrating the operation of the textured implant device as shown in

FIGS. 12-14;

DETAILED DESCRIPTION OF THE PREFERRED EMBODIMENT

Figure 1:
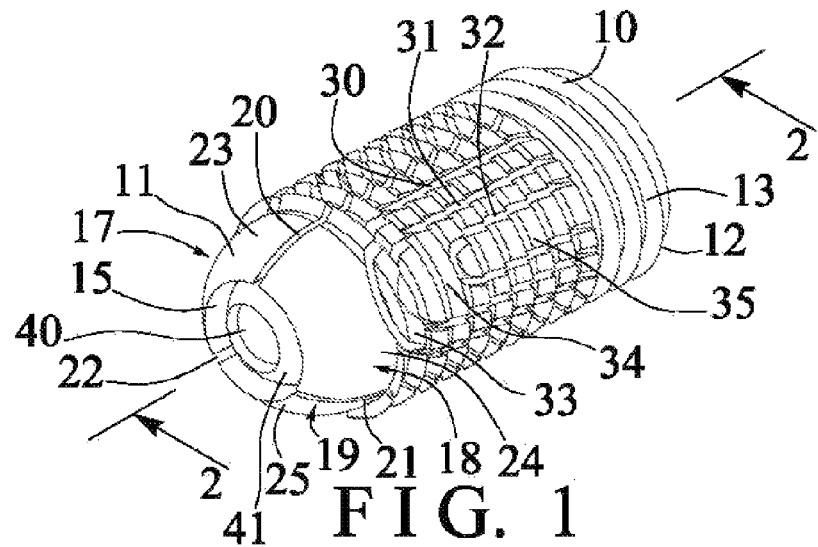
FIG. 1 is a perspective view of a textured bone graft or implant device in accordance with the present invention, for fitting or engaging into the bone materials or members of the user.

Referring to the drawings, and initially to FIGS. 1-9, a textured bone graft or implant device in accordance with the present invention is generally provided for being filled or fitted or engaged into the damaged or degenerated bone materials or members, such as the mandible, the spinal column or vertebrae of a human or user (not illustrated), or the like for repairing bone defects, for example, the textured implant device may be directly engaged into the damaged or degenerated portion of the bone materials (not illustrated), or may be disposed or attached or mounted or secured or engaged into the space between two vertebral bodies (not illustrated) for forming or acting as the intervertebral disk and for sustain the vertebral bodies in place.

For example, the textured implant device comprises a constructed or textured three dimensional or spatial inner or insert or core structure or body or housing member 10 made into various kinds of different structures or configurations or shapes, such as a tubular or cylindrical shaped structure as shown in FIGS. 1-11, a substantially rectangular shaped structure as shown in FIGS. 12-23, or other shaped structures. However, the rectangular or other shaped structure as shown in FIGS. 12-23 is provided for illustrative purposes only and forming no part of the claimed invention. The constructed or textured three dimensional or spatial inner or insert or body structure or core or body or housing member 10 is made or manufactured or formed with various kinds of relatively stronger materials, such as metal, stainless steel, titanium, gold, silver, stellite, oxidized cobalt, tantalum, or other metal materials, china or porcelain materials, poly ethylene (PE), poly urethane (PU), silicon or molecular components or polymer materials.

For example, as shown in FIGS. 1-11, the housing member 10 includes a cylindrical shaped structure preferably having a relatively reduced or narrowed or rounded first end 11 for being easily and quickly engaged into the space between two vertebral bodies (not illustrated), for example, and having a relatively greater second end 12. It is preferable, but not necessary that the housing member 10 includes a rough or serrated outer peripheral portion or surface 13 for frictionally contacting or engaging with the vertebral bodies (not illustrated) and for allowing the housing member 10 to be solidly and stably attached or mounted or anchored or retained or secured or positioned between the vertebral bodies, and for preventing the housing member 10 from being moved or slip relative to vertebral bodies.

The housing member 10 includes a longitudinal hole or bore 14 formed therein and disposed or positioned or located closer to the second end 12 but not formed through the first end 11 of the housing member 10 for pivotally or rotatably receiving or engaging with a fastener or bolt or screw 40 therein, and includes a longitudinal passage or conduit 15 formed therein and disposed or positioned or located closer to the first end 11 but not formed through the second end 12 of the housing member 10, and the conduit 15 of the housing member 10 includes an inner diameter greater than that of the bore 14 of the housing member 10 for slidably receiving or engaging with a follower or actuator 41 having a circular or spherical structure therein, and for guiding the actuator 41 to slide along the conduit 15 of the housing member 10 only, and for preventing the actuator 41 from pivoting or rotating relative to the housing member 10.

The housing member 10 further includes an enlarged space or chamber or compartment 16 formed in the second end 12 of the housing member 10 and communicating with the bore 14 of the housing member 10 for pivotally or rotatably receiving or engaging with an enlarged head 42 of the screw 40 and for anchoring or securing or retaining or positioning the screw 40 within the bore 14 of the housing member 10, and for preventing the screw 40 from moving axially or longitudinally relative to the housing member 10. The screw 40 normally includes an engaging recess or depression or hole formed therein (not illustrated) for receiving or engaging with a screw driving tool (not illustrated) and for allowing the screw 40 to be pivoted or rotated relative to the housing member 10, and thus for allowing the actuator 41 that is threaded or engaged with the screw 40 to be forced to move toward or away from the head 42 of the screw 40.

As shown in FIGS. 1 and 7-9, the housing member 10 includes two or more (such as three) equally spaced or divided portions or sectors or areas or segments or sections 17, 18, 19 each occupying about sixty (60) degrees. For example, as shown in FIG. 1, the housing member 10 includes two or more (such as three) equally spaced grooves or channels or slots 20, 21, 22 longitudinally formed therein and disposed or positioned or located closer to the first end 11 but not formed through the second end 12 of the housing member 10 for forming or defining the equally spaced or divided sections 17, 18, 19 of the housing member 10, and for forming or defining the resilient or spring arms or blades or branches 23, 24, 25 in the sections 17, 18, 19 of the housing member 10 respectively. Alternatively, as shown in FIGS. 10 and 11, the housing member 101 may include no dividing slots therein and may also include two or more (such as three) equally spaced or divided sections 17, 18, 19 therein.

Further alternatively, as shown in FIGS. 12-23, the housing member 102, 103 may include two opposite portions or sectors or areas or segments or sections each occupying about ninety (90) degrees having two opposite and resilient or spring arms or blades or branches formed or provided therein, which will be illustrated and described hereinafter; similarly, the housing member may also include four or more equally spaced or divided portions or sectors or areas or segments or sections having the equally spaced or divided resilient or spring arms or blades or branches formed or provided therein (not illustrated). Referring again to FIGS. 1-9, the housing member 10 further includes one or more (such as three) slots or channels or grooves 30, 31, 32, such as U-shaped grooves 30-32 formed or provided in each of the sections 17-19 and/or the spring branches 23-25 of the housing member 10 and spaced or separated or offset from each other for forming or defining one or more (such as three) spaced or separated or divided resilient or spring legs or arms or limbs or blades 33, 34, 35, such as U-shaped blades 33-35 in the respective section 17-19 of the housing member 10, and the blades 33-35 each include a tilted or inclined operating or actuating or guiding surface or member 36, 37, 38, best shown in FIGS. 2-6, extended into the conduit 15 of the housing member 10 for selectively engaging with the actuator 41 which may selectively engage with and force the blades 33-35 to move radially and outwardly (FIGS. 4-6, 8-9) to engage with the vertebral bodies.

As also shown in FIGS. 2-6, the first guiding member 36 of the first blade 33 of the respective section 17-19 of the housing member 10 preferably, but not necessary includes an inner diameter greater than that of the other guiding members 37, 38, and disposed or positioned or located closer to the actuator 41, and arranged for allowing the first guiding member 36 of the first blade 33 to be firstly contacted or engaged with the actuator 41 (FIG. 3) and to be firstly and selectively forced to move radially and outwardly to engage with the vertebral bodies. Similarly, the second guiding member 37 of the second blade 34 preferably, but not necessary includes an inner diameter greater than that of the other guiding members 38, and disposed or positioned or located closer to the actuator 41 than the third or other guiding members 38, and arranged for allowing the second guiding member 37 of the second blade 34 to be contacted or engaged with the actuator 41 (FIG. 4) and to be selectively forced to move radially and outwardly to engage with the vertebral bodies before the third or other guiding members 38 the third or other blades 35 are contacted or engaged with and actuated or operated by the actuator 41.

Figure 2:
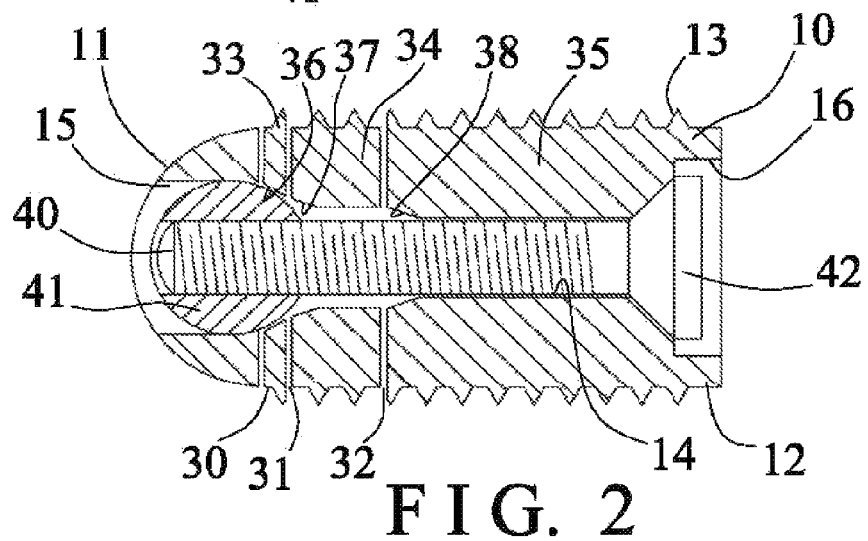
FIG. 2 is a cross sectional view of the textured implant device, taken along lines 2-2 of FIG. 1.
Figure 3:
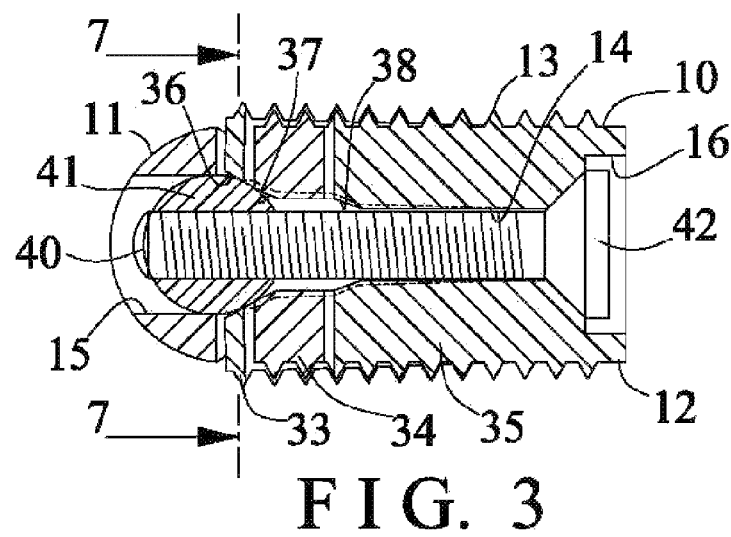
FIGS. 3, 4, 5, 6 are other cross sectional views similar to FIG. 2, illustrating the operation of the textured implant device.
Figure 4:
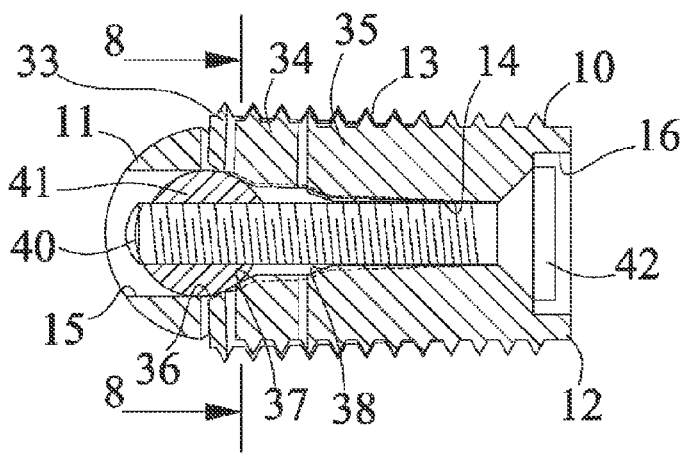
Figure 5:
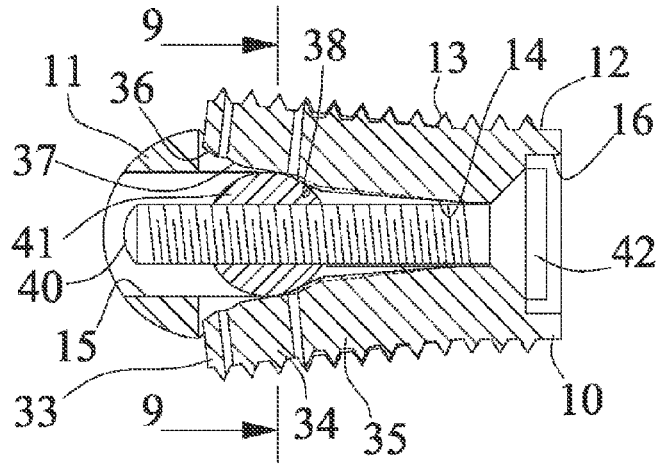
Figure 6:
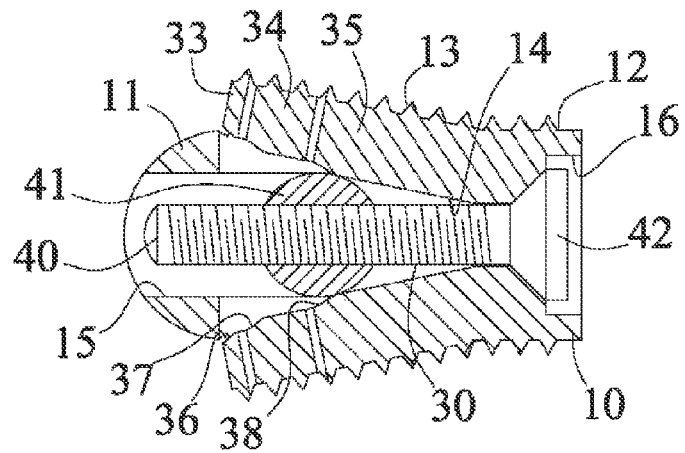
Figure 14:
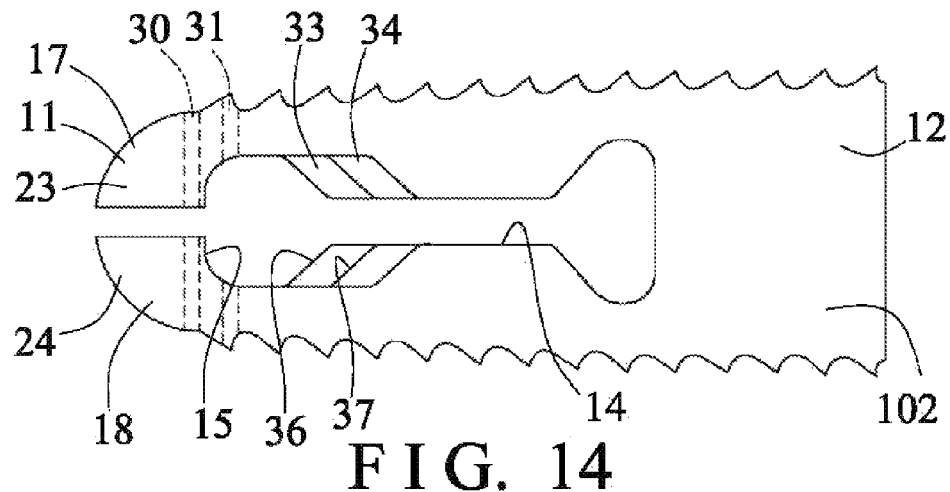
FIG. 14 is a side plan schematic view of the textured implant device as shown in FIG. 12.
Figure 15:
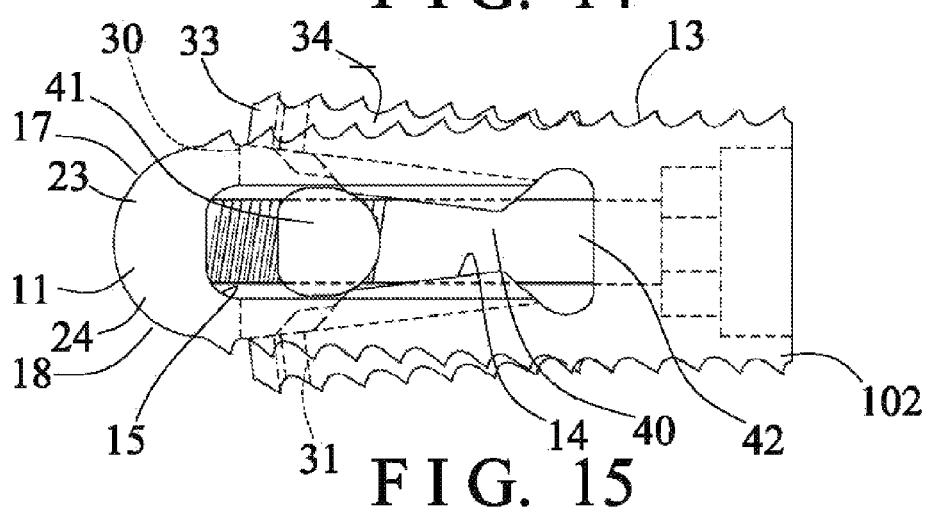
Figure 16:
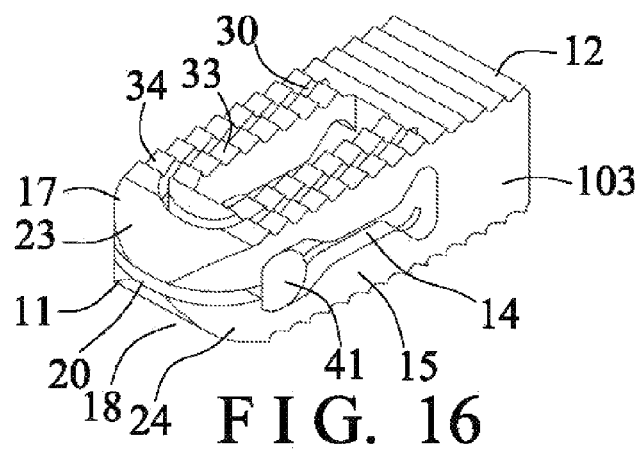
FIG. 16 is a still further perspective view similar to FIGS. 1, 10 and 12, illustrating the still further arrangement of the textured implant device.
Figure 17:
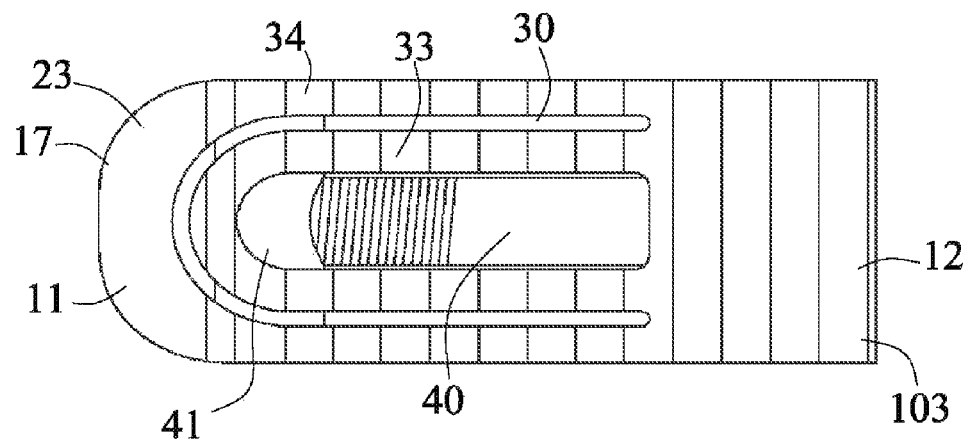
FIG. 17 is a top plan schematic view of the textured implant device as shown in FIG. 16.
Figure 18:
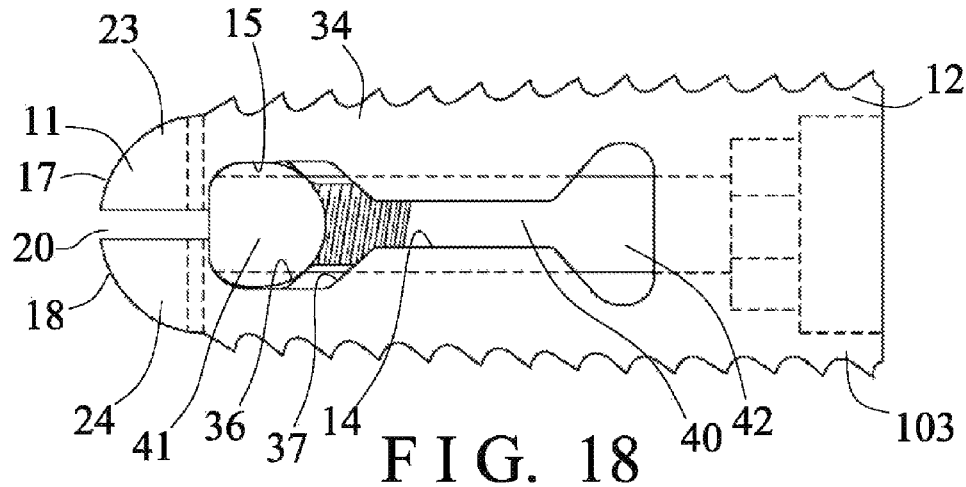
FIG. 18 is a side plan schematic view of the textured implant device as shown in FIGS. 16-17.
Figure 19:
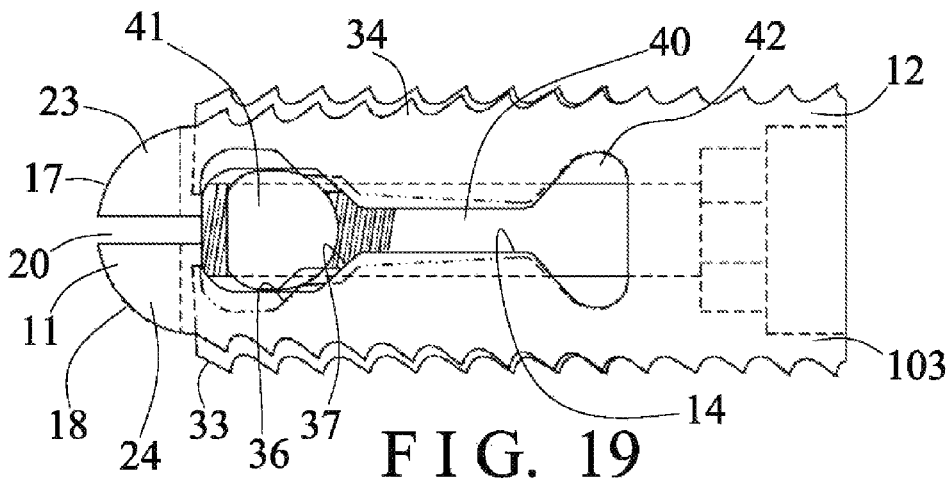
FIGS. 19, 20, 21 are side plan schematic views similar to FIG. 18, illustrating the operation of the textured implant device as shown in FIGS. 16-18.
Figure 20:
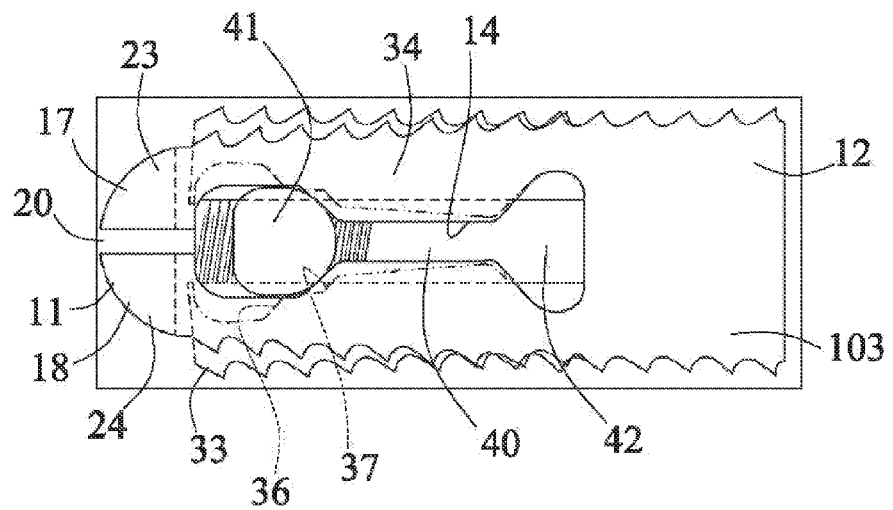
Figure 21:
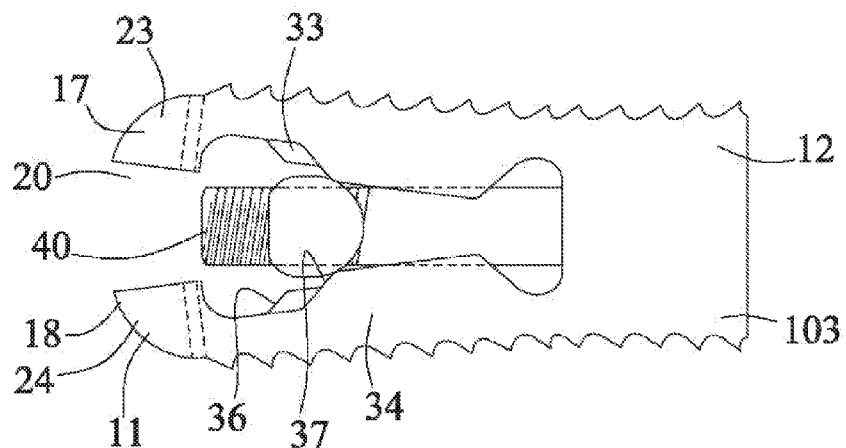
Figure 22:
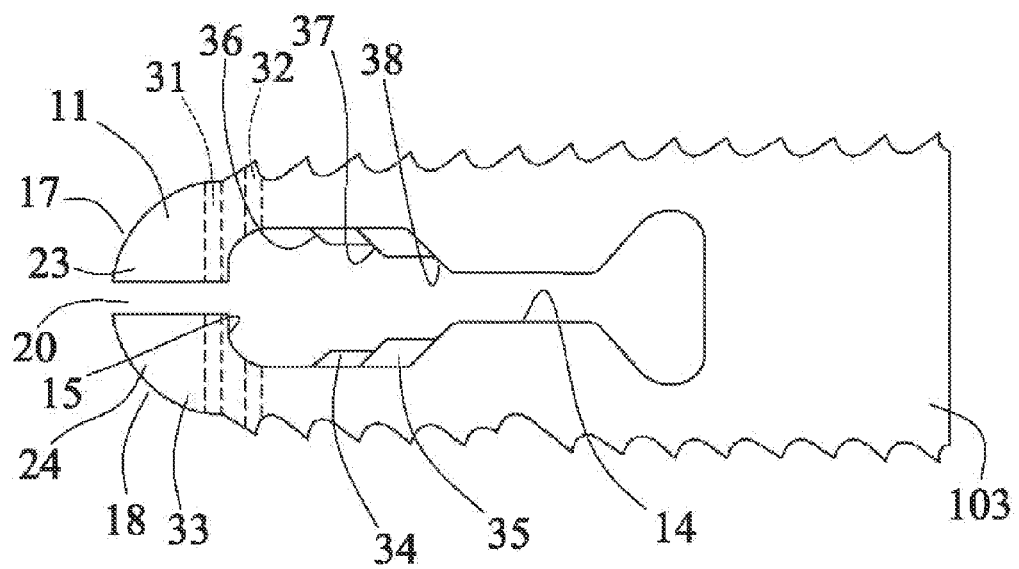
FIGS. 22, 23 are other side plan schematic views similar to FIGS. 18-21, illustrating the still further arrangements of the textured implant device.
Figure 23:
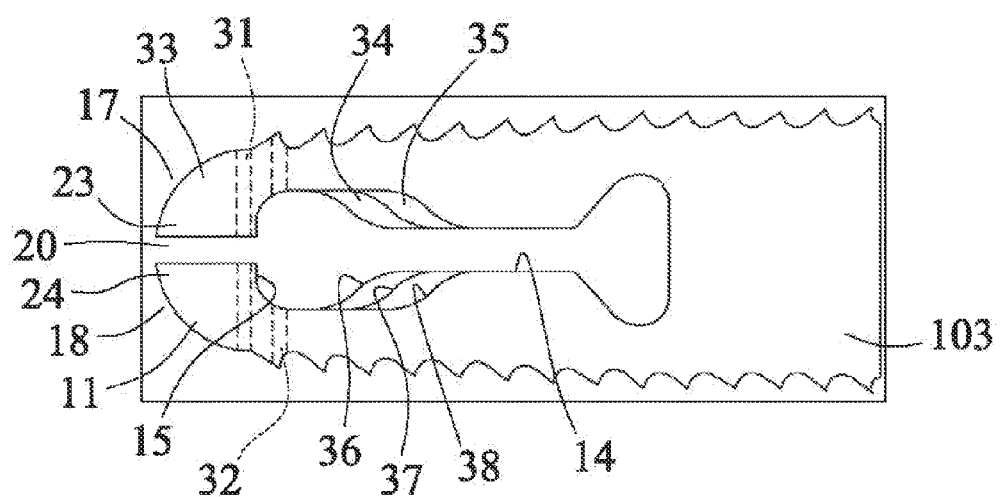

In operation, as shown in FIGS. 2 and 3, the relatively reduced or narrowed or rounded first end 11 of the housing member 10 is arranged for allowing the housing member 10 to be easily and quickly engaged into the space between two vertebral bodies, after the housing member 10 has been engaged into the space between two vertebral bodies, the screw 40 may be pivoted or driven to rotate relative to the housing member 10 with the screw driving tool (not illustrated), in order to guide and force the actuator 41 to slide or to move along the conduit 15 of the housing member 10 and to firstly contact or engage with the first guiding member 36 of the first blade 33 (FIG. 3), and to firstly and selectively force the first guiding member 36 to move radially and outwardly to engage with the vertebral bodies.

The actuator 41 may than further be moved toward the head 42 of the screw 40 when the screw 40 is further pivoted or driven or rotated relative to the housing member 10, in order to guide and force the actuator 41 to then contact or engage with the second guiding member 37 of the second blade 34 (FIG. 4) and to selectively force the second guiding member 37 of the second blade 34 to move radially and outwardly to engage with the vertebral bodies, and the actuator 41 may then be contacted or engaged with the third guiding member 38 of the third blade 35 (FIGS. 5, 6) when the actuator 41 is further moved toward the head 42 of the screw 40 with or by the screw 40, such that the resilient or spring blades 33-35 may be moved radially and outwardly to engage with the vertebral bodies in sequence or in series according to the damage status or condition of the vertebral bodies.

Alternatively, as shown in FIGS. 12-15, the housing member 102 may include two opposite portions or sectors or areas or segments or sections 17, 18 each occupying about ninety (90) degrees having two opposite and resilient or spring arms or blades or branches 23, 24 formed or provided therein, and each section 17, 18 or each branch 23, 24 includes two or more grooves 30, 31, such as U-shaped grooves 30-31 formed or provided in each of the sections 17-18 and/or the spring branches 23-24 of the housing member 102 and spaced or separated or offset from each other for forming or defining two or more spaced or separated or divided resilient or spring legs or arms or limbs or blades 33, 34, such as U-shaped blades 33-34 in the respective section 17-18 of the housing member 102, and the blades 33-34 each also include a tilted or inclined operating or actuating or guiding surface or element or member 36, 37 (FIGS. 14-15) extended into the conduit 15 of the housing member 102 for selectively engaging with the actuator 41 which may selectively engage with and force the blades 33-34 to move radially and outwardly and to engage with the vertebral bodies.

Further alternatively, as shown in FIGS. 16-23, the housing member 103 may include a groove or channel or slot 20 formed therein and disposed or positioned or located closer to the first end 11 but not formed through the second end 12 of the housing member 103 for forming or defining the equally spaced or divided or opposite sections 17, 18 of the housing member 103, and for forming or defining the resilient or spring arms or blades or branches 23, 24 in the sections 17, 18 of the housing member 103 respectively. The housing member 103 may include a single groove 30, such as U-shaped groove 30 formed or provided in each of the sections 17-18 and/or the spring branches 23-24 of the housing member 103 for forming or defining two or more spaced or separated or divided resilient or spring legs or arms or limbs or blades 33, 34, such as U-shaped blades 33-34 in the respective section 17-18 of the housing member 103.

Similarly, the blades 33-34 each may also include a tilted or inclined (FIGS. 18-20) or curved or rounded (FIG. 23) or ladder-shaped (FIGS. 21, 22) operating or actuating or guiding surface or member 36, 37 (FIGS. 18-23) extended into the conduit 15 of the housing member 103 for selectively engaging with the actuator 41 which may selectively engage with and force the blades 33-34 to move radially and outwardly and to engage with the vertebral bodies. As shown in FIGS. 18-23, the guiding members 36, 37 and/or the blades 33-34 may include various kinds of different structures or configurations or shapes and/or tilts or inclinations for suitably engaging with the actuator 41 and for allowing the actuator 41 to easily and effectively actuate or operate the guiding members 36, 37 and thus the blades 33-34 to engage with the vertebral bodies.

Accordingly, the textured implant device in accordance with the present invention includes an improved structure for being suitably filled or fitted or engaged into the bone materials or members of the human or user and for repairing bone defects, such as the damaged or degenerated spinal disc in a spinal column or vertebrae of a human or user, or the like.

Although this invention has been described with a certain degree of particularity, it is to be understood that the present disclosure has been made by way of example only and that numerous changes in the detailed construction and the combination and arrangement of parts may be resorted to without departing from the spirit and scope of the invention as hereinafter claimed.

I claim:

1. A textured implant device comprising:

a housing member including a first end and a second end, and including a longitudinal bore formed in said housing member and located closer to said second end than it is to the first end, and including a longitudinal conduit formed in said housing member and located closer to said first end than it is to the second end but not formed through said second end of said housing member, and said conduit of said housing member including an inner diameter greater than that of said bore of said housing member, an actuator slidably received and engaged in said conduit of said housing member, and a screw rotatably received and engaged in said bore of said housing member and threaded and engaged with said actuator, and said housing member including a first section and at least one additional section equally spaced from each other about a central longitudinal axis of the housing member, and including a groove formed in each section of said housing member for forming and defining a first blade and at least one additional blade in each section of said housing member, and said first and said at least one additional blade each including a guiding member extended into said conduit of said housing member for selectively engaging with said actuator, said guiding member of said first blade being located closer to said actuator than said guiding member of said at least one additional blade, and said actuator being contacted and engaged with said guiding member of said first blade before contacting or engaging with said guiding member of said at least one additional blade in order to force said first blade to move radially and outwardly of said housing member before forcing said at least one additional blade to move radially and outwardly of said housing member.

2. The textured implant device as claimed in claim 1, wherein each groove of said housing member is U-shaped for forming and defining a U-shaped first blade and a U-shaped at least one additional blade in each section of said housing member.

3. The textured implant device as claimed in claim 1, wherein said housing member includes at least one slot formed therein and located closer to said first end than it is to the second end but not formed through said second end of said housing member for forming and defining said equally spaced first and at least one additional sections of said housing member and for forming and defining a first branch and at least one additional branch in said first and at least one additional section of said housing member respectively.

4. The textured implant device as claimed in claim 1, wherein said first end of said housing member includes a rounded structure.

5. The textured implant device as claimed in claim 1, wherein each of said guiding members of said first and at least one additional blade is selected from a tilted, inclined, curved, rounded, and ladder-shaped guiding member.

6. The textured implant device as claimed in claim 1, wherein said actuator includes a spherical structure.

* * * * *